United States Patent
Conejo Castano et al.

(10) Patent No.: US 12,036,169 B2
(45) Date of Patent: Jul. 16, 2024

(54) PATIENT LIFT SLING

(71) Applicant: Liko Research & Development AB, Lulea (SE)

(72) Inventors: Alejandro Noe Conejo Castano, Batesville, IN (US); Michael Buccieri, Greenfield, IN (US); Morgan Dreyer, Versailles, IN (US); Elin K. Dovervik, Luela (SE); Jennifer D. Slavin, Batesville, IN (US); Edward J. Koors, Indianapolis, IN (US)

(73) Assignee: Liko Research & Development AB, Lulea (SE)

( * ) Notice: Subject to any disclaimer, the term of this patent is extended or adjusted under 35 U.S.C. 154(b) by 405 days.

(21) Appl. No.: 17/376,262

(22) Filed: Jul. 15, 2021

(65) Prior Publication Data

US 2022/0015972 A1    Jan. 20, 2022

Related U.S. Application Data

(60) Provisional application No. 63/053,855, filed on Jul. 20, 2020.

(51) Int. Cl.
| A61G 7/00 | (2006.01) |
| A61F 13/42 | (2006.01) |
| A61F 13/76 | (2006.01) |
| A61G 7/10 | (2006.01) |
| A61F 13/56 | (2006.01) |

(52) U.S. Cl.
CPC ............ *A61G 7/1051* (2013.01); *A61F 13/42* (2013.01); *A61F 13/76* (2013.01); *A61G 7/1015* (2013.01); *A61F 2013/424* (2013.01); *A61F 2013/5661* (2013.01); *A61G 2203/10* (2013.01)

(58) Field of Classification Search
CPC .......... A61G 7/00; A61G 7/10; A61G 7/1049; A61G 7/1051; A61F 13/42; A61F 13/76; A61F 2013/424; A61F 2013/5661
See application file for complete search history.

(56) References Cited

U.S. PATENT DOCUMENTS

| 2,835,902 | A | * | 5/1958 | Fash ........................ A61G 1/01 5/81.1 T |
| 4,675,925 | A | | 6/1987 | Littleton |
| 5,086,530 | A | * | 2/1992 | Blake ................... A47C 31/105 5/500 |

(Continued)

FOREIGN PATENT DOCUMENTS

| CA | 3044312 A1 | 11/2019 |
| DE | 202006011546 U | 10/2006 |

(Continued)

OTHER PUBLICATIONS

European Search Report dated Dec. 13, 2021.

*Primary Examiner* — Fredrick C Conley
(74) *Attorney, Agent, or Firm* — Barnes & Thornburg LLP

(57) ABSTRACT

A person lift system includes a motor and a sling bar coupled to the motor. The sling bar includes a first attachment hook at a first end region of the sling bar and a second attachment hook at a second end region of the sling bar. A patient-lift sling includes a sling body and a plurality of attachment straps coupled to the sling body. Each of the plurality of attachment straps is configured to attach to one of the plurality of attachment hooks.

19 Claims, 10 Drawing Sheets

(56) References Cited

U.S. PATENT DOCUMENTS

| | | | |
|---|---|---|---|
| 5,530,975 A | 7/1996 | Firebaugh et al. | |
| 6,073,280 A * | 6/2000 | Farnum | A62B 35/0025 |
| | | | 5/89.1 |
| 9,808,387 B2 | 11/2017 | Love et al. | |
| 9,833,371 B2 | 12/2017 | Purdy et al. | |
| 10,213,349 B2 | 2/2019 | Solomon | |
| 10,251,492 B2 | 4/2019 | Waters et al. | |
| 10,398,614 B2 | 9/2019 | Rigoni et al. | |
| 10,918,548 B2 | 2/2021 | Olsson et al. | |
| 2002/0070868 A1 * | 6/2002 | Jeutter | A61F 13/42 |
| | | | 340/604 |
| 2012/0000876 A1 | 1/2012 | Bergenstrale et al. | |
| 2013/0117908 A1 | 5/2013 | Dyson | |
| 2013/0152304 A1 * | 6/2013 | Dovervik | A61G 7/1051 |
| | | | 5/89.1 |
| 2015/0052680 A1 * | 2/2015 | Brandorff | A61G 7/1051 |
| | | | 5/89.1 |
| 2015/0052681 A1 * | 2/2015 | Hagler | A61G 7/1051 |
| | | | 5/89.1 |
| 2015/0074903 A1 * | 3/2015 | Berg | A47G 9/0238 |
| | | | 5/83.1 |
| 2015/0216751 A1 | 8/2015 | Stokes et al. | |
| 2016/0095777 A1 * | 4/2016 | Berman | A61G 7/1026 |
| | | | 5/81.1 T |
| 2016/0374883 A1 * | 12/2016 | Galbraith | A61G 7/1073 |
| | | | 5/81.1 T |
| 2018/0185225 A1 | 7/2018 | Arjohuntleigh | |

FOREIGN PATENT DOCUMENTS

| | | | | |
|---|---|---|---|---|
| EP | 0095325 B1 | 11/1983 | | |
| EP | 2604241 | 6/2013 | | |
| EP | 2570106 A3 | 6/2014 | | |
| EP | 2979673 | 2/2016 | | |
| EP | 3009118 A1 | 4/2016 | | |
| EP | 3069704 | 4/2018 | | |
| GB | 2303331 A * | 2/1997 | | A61G 7/1051 |
| GB | 2303331 A | 2/1997 | | |
| GB | 2466304 | 6/2010 | | |
| GB | 2531276 A | 4/2016 | | |
| JP | 2006263314 | 10/2006 | | |
| WO | 2010020818 | 2/2010 | | |

* cited by examiner

PATIENT LIFT SLING

PRIORITY CLAIM

This application claims priority under 35 U.S.C. § 119(e) to U.S. Provisional Application Ser. No. 63/053,855, filed Jul. 20, 2020, which is expressly incorporated by reference herein.

BACKGROUND

The present disclosure relates to patient lift systems and particularly, to patient lift systems having a patient-lift sling that can be attached to a sling bar and raised and lowered by a lift. More particularly, the present disclosure relates to a patient-lift sling that is constructed to increase comfort for the patient and provide increased ergonomics for caregivers.

Patient lift systems generally include a motor coupled to a sling bar to raise and lower the sling bar. A sling is attached to the sling bar and is configured to support and suspend a patient from the sling bar. The patient is raised and lowered in the sling by activating the motor. Such patient lift systems are sometimes used to move patients onto and off of patient support apparatuses. To attach the sling to the sling bar, loops of the sling are coupled to attachment hooks of the sling bar. Some slings are made from a relatively stiff fabric that can cause uncomfortable pressure or pinch points on the patient while the patient being held by the sling is raised and lowered by a lift.

Slings sometimes include features like handles and pockets to help caregivers fit the sling to a patient. Such handles and pockets may be located in areas that are hard to access and could result in the sling being improperly applied on the patient which may contribute to uncomfortable pressure and pinch points.

Therapies that use slings may require a patient to spend a prolonged period of time in the sling. Some patient's requiring use of a sling may be incontinent and could have an incontinence event while using a sling. Some slings may be washable to clean the sling after an incontinence event, but this could result in longer wait times between uses of the sling.

SUMMARY

The present disclosure includes one or more of the features recited in the appended claims and/or the following features which, alone or in any combination, may comprise patentable subject matter.

In accordance with a first aspect of the present disclosure, a patient-lift sling includes a sling body, a perimeter binding, and a plurality of attachment straps. The sling body is configured to support a patient. The perimeter binding extends around an outer edge of the sling body, The plurality of attachment straps are coupled to the perimeter binding.

In some embodiments, the sling body includes at least one layer of warp-knit fabric that has a first stiffness value and the perimeter binding and each of the attachment straps include at least one layer of woven fabric that has a second stiffness value greater than the first stiffness value.

In some embodiments, the sling body includes a body section configured to support at least a portion of a patient's upper body, a first leg section configured to support one of the patient's legs, and a second leg section configured to support another of the patient's legs.

In some embodiments, the sling body includes a first layer of warp-knit fabric, a second layer of warp-knit fabric at least partially spaced apart from the first layer of warp-knit fabric, and an inner layer of spacer material arranged between the first and second layers of warp-knit fabric.

In some embodiments, the spacer material includes an upper-body portion located in the body section, a first leg portion coupled with the upper-body section and located in the first leg section, and a second leg portion coupled with the upper-body section and located in the second leg section.

In some embodiments, the sling body further comprises a plurality of stitches that extend through the first layer of warp-knit fabric, the spacer material, and the second layer of warp-knit fabric, and wherein the stitches are oriented relative to one another to maximize flexibility of the sling body.

In some embodiments, the plurality of stitches includes a plurality of vertically oriented stitches located on the body section, a plurality of horizontally-oriented stitches located on the first and second leg sections, and at least one diagonally-oriented stitch located between the vertically-oriented stitches and the first leg section and between the vertically-oriented stitches and the second leg section.

In some embodiments, the vertically-oriented stitches include a first vertical stitch that is configured to align with a patient's spine.

In some embodiments, the vertically-oriented stitches further includes a second vertical stitch that is configured to align with the patient's left shoulder blade, and a third vertical stitch that is configured to align with the patient's right shoulder blade.

In some embodiments, the sling body has a first color and each of the vertically-oriented stitches has a second color different than the first color.

In some embodiments, the plurality of attachment straps includes a first set of body-section loops coupled to the perimeter binding at each upper corner of the body section and a second set of body-section loops coupled to the perimeter binding and spaced inward from the first set of body-section loops.

In some embodiments, the sling further comprises a body-section adjustment system configured to change a width of the body section to raise and lower a patient's head.

In some embodiments, body section has a first upper corner and a second upper corner and the adjustment system includes a first extensible-strap unit coupled to the perimeter binding and interconnecting the first outer corner of the body section and a first point on the perimeter binding between the first upper corner and the second upper corner and a second extensible-strap unit coupled to the perimeter binding and interconnecting the second outer corner of the body section and a second point on the perimeter binding between the first point and the second upper corner.

In some embodiments, the first and second extensible-strap units each include a first strap coupled to one of the first upper corner and the second upper corner, a second strap coupled to a corresponding one of the first point and the second point and a buckle coupled to the first strap and the second strap and configured to allow adjustment of at least one of the first strap and the second strap to raise and lower a head section of the sling body.

In some embodiments, the body section is formed to include a first cutout along a first lateral side of the body section and a second cutout along a second lateral side of the body section.

In some embodiments, an edge of the body section defining the first cutout and the second cutout is spaced apart from the perimeter binding to provide a first handle on the first lateral side and a second handle on the second lateral side.

In some embodiments, the first handle and the second handle are the only handles on the body portion.

In some embodiments, the sling body, the perimeter binding, and the plurality of attachment straps are all made from a material consisting of polyester.

In some embodiments, the sling further comprises an incontinence pad coupled removably to sling body by a plurality of adhesive strips that extend parallel with one another along a length of the sling body.

In some embodiments, the incontinence pad includes a first side flange and a second side flange on an opposite side of the incontinence pad as the first side flange and wherein the first and second side flanges are coupled to an underside of the sling body by an adhesive strip.

In some embodiments, the incontinence pad includes a at least one electrical trace fitted within the incontinence pad and a transponder tag coupled to the at least one electrical trace to provide a signal in response to moisture being present on the incontinence pad to notify a caregiver that an incontinence event has occurred.

According to a second aspect of the present disclosure, a patient-lift sling includes a body section, a first leg section and a second leg section. The body section is configured to support at least a portion of a patient's upper body. The first leg section is configured to support one of the patient's legs. The second leg section is configured to support another of the patient's legs.

In some embodiments, the body section includes a body portion that has a first stiffness, a first interface portion between the body portion and the first leg section, and a second interface portion between the body portion and the second leg section, the first interface portion and the second interface portion each have a second stiffness that is less that the first modulus of elasticity of the body portion.

In some embodiments, the body portion is formed to include a first cutout along a first lateral side of the body portion and a second cutout along a second lateral side of the body portion.

In some embodiments, the body section, the first leg section, and the second leg section are connected to one another by a perimeter binding.

In some embodiments, an edge of the body portion defining the first cutout and the second cutout is spaced apart from the perimeter binding to provide a first handle on the first lateral side and a second handle on the second lateral side.

In some embodiments, the first handle and the second handle are the only handles on the body portion.

In some embodiments, the body section, the first leg section, and the second leg section are all made from a material consisting of polyester.

In some embodiments, the sling further comprises a layer of spacer material that is arranged to lie on a front side of at least one of the body section, the first leg section, and the second leg section.

In some embodiments, the layer of spacer material includes a first patch arranged to lie on the body portion, a second patch spaced apart from the first patch and arranged to lie on the first leg section, and a third patch spaced apart from the first patch and the second patch and arranged to lie on the second leg section.

In some embodiments, the first patch extends from an upper edge of the body portion to a lower edge of the body portion and is tied together with the body portion at the upper edge and the lower edge so that the first patch reinforces the body portion.

In some embodiments, the body portion includes a first pocket, the first leg section includes a second pocket, and the second leg section includes a third pocket.

In some embodiments, the sling further comprises an incontinence pad coupled removably to at least one of the body section, the first leg section, and the second leg section.

In some embodiments, the incontinence pad includes a non-woven top sheet, an absorbent core, and a fluid-impermeable back sheet.

In some embodiments, the back sheet is coupled to the at least one of the body section, the first leg section, and the second leg section by a plurality of adhesive strips.

In some embodiments, the back sheet is coupled to the at least one of the body section, the first leg section, and the second leg section by a plurality of straps.

In accordance with a third aspect of the present disclosure, a patient-lift sling includes a sling body configured to support a patient above ground, a plurality of attachment straps that extend from the body support, and a disposable incontinence pad removably coupled with the sling body by a plurality of adhesive strips that attach the incontinence pad to a top side of the sling body and an underside of the sling body.

In some embodiments, the incontinence pad includes a non-woven top sheet, an absorbent core, a fluid-impermeable back sheet.

In some embodiments, the sling body includes at least one layer of warp-knit fabric that has a first stiffness value and the perimeter binding and each of the attachment straps include at least one layer of woven fabric that has a second stiffness value greater than the first stiffness value.

In some embodiments, the sling body includes a body section configured to support at least a portion of a patient's upper body, a first leg section configured to support one of the patient's legs, and a second leg section configured to support another of the patient's legs.

In some embodiments, the sling body includes a first layer of warp-knit fabric, a second layer of warp-knit fabric at least partially spaced apart from the first layer of warp-knit fabric, and an inner layer of spacer material arranged between the first and second layers of warp-knit fabric.

In some embodiments, the spacer material includes an upper-body portion located in the body section, a first leg portion coupled with the upper-body section and located in the first leg section, and a second leg portion coupled with the upper-body section and located in the second leg section.

In some embodiments, the sling body further comprises a plurality of stitches that extend through the first layer of warp-knit fabric, the spacer material, and the second layer of warp-knit fabric, and wherein the stitches are oriented relative to one another to maximize flexibility of the sling body.

In some embodiments, the plurality of stitches includes a plurality of vertically oriented stitches located on the body section, a plurality of horizontally-oriented stitches located on the first and second leg sections, and at least one diagonally-oriented stitch located between the vertically-oriented stitches and the first leg section and between the vertically-oriented stitches and the second leg section.

In some embodiments, the vertically-oriented stitches include a first vertical stitch that is configured to align with a patient's spine.

In some embodiments, the vertically-oriented stitches further includes a second vertical stitch that is configured to align with the patient's left shoulder blade, and a third vertical stitch that is configured to align with the patient's right shoulder blade.

In some embodiments, the sling body has a first color and each of the vertically-oriented stitches has a second color different than the first color.

In some embodiments, the plurality of attachment straps includes a first set of body-section loops coupled to the perimeter binding at each upper corner of the body section and a second set of body-section loops coupled to the perimeter binding and spaced inward from the first set of body-section loops.

In some embodiments, the sling further comprises a body-section adjustment system configured to change a width of the body section to raise and lower a patient's head.

In some embodiments, body section has a first upper corner and a second upper corner and the adjustment system includes a first extensible-strap unit coupled to the perimeter binding and interconnecting the first outer corner of the body section and a first point on the perimeter binding between the first upper corner and the second upper corner and a second extensible-strap unit coupled to the perimeter binding and interconnecting the second outer corner of the body section and a second point on the perimeter binding between the first point and the second upper corner.

In some embodiments, the first and second extensible-strap units each include a first strap coupled to one of the first upper corner and the second upper corner, a second strap coupled to a corresponding one of the first point and the second point and a buckle coupled to the first strap and the second strap and configured to allow adjustment of at least one of the first strap and the second strap to raise and lower a head section of the sling body.

In some embodiments, the body section is formed to include a first cutout along a first lateral side of the body section and a second cutout along a second lateral side of the body section.

In some embodiments, an edge of the body section defining the first cutout and the second cutout is spaced apart from the perimeter binding to provide a first handle on the first lateral side and a second handle on the second lateral side.

In some embodiments, the first handle and the second handle are the only handles on the body portion.

In some embodiments, the sling body, the perimeter binding, and the plurality of attachment straps are all made from a material consisting of polyester.

In some embodiments, the incontinence pad is coupled removably to the sling body by a plurality of adhesive strips that extend parallel with one another along a length of the sling body.

In some embodiments, the incontinence pad includes a first side flange and a second side flange on an opposite side of the incontinence pad as the first side flange and wherein the first and second side flanges are coupled to an underside of the sling body by an adhesive strip.

In some embodiments, the incontinence pad includes a at least one electrical trace fitted within the incontinence pad and a transponder tag coupled to the at least one electrical trace to provide a signal in response to moisture being present on the incontinence pad to notify a caregiver that an incontinence event has occurred.

In some embodiments, the incontinence pad has an hourglass shape when viewed from above.

In accordance with a fourth aspect of the present disclosure, a patient-lift sling includes a sling body configured to support a patient above ground, a perimeter binding coupled to an outer edge of the sling body, and a plurality of attachment straps that extend from the perimeter binding. In some embodiments, the sling body is made from a highly-stretchable fabric.

In some embodiments, the sling body includes a body section configured to support at least a portion of a patient's upper body, a first leg section configured to support one of the patient's legs, and a second leg section configured to support another of the patient's legs.

In some embodiments, the sling body includes a first layer of warp-knit fabric, a second layer of warp-knit fabric at least partially spaced apart from the first layer of warp-knit fabric, and an inner layer of spacer material arranged between the first and second layers of warp-knit fabric.

In some embodiments, the spacer material includes an upper-body portion located in the body section, a first leg portion coupled with the upper-body section and located in the first leg section, and a second leg portion coupled with the upper-body section and located in the second leg section.

In some embodiments, the sling body further comprises a plurality of stitches that extend through the first layer of warp-knit fabric, the spacer material, and the second layer of warp-knit fabric, and wherein the stitches are oriented relative to one another to maximize flexibility of the sling body.

In some embodiments, the plurality of stitches includes a plurality of vertically oriented stitches located on the body section, a plurality of horizontally-oriented stitches located on the first and second leg sections, and at least one diagonally-oriented stitch located between the vertically-oriented stitches and the first leg section and between the vertically-oriented stitches and the second leg section.

In some embodiments, the vertically-oriented stitches include a first vertical stitch that is configured to align with a patient's spine.

In some embodiments, the vertically-oriented stitches further includes a second vertical stitch that is configured to align with the patient's left shoulder blade, and a third vertical stitch that is configured to align with the patient's right shoulder blade.

In some embodiments, the sling body has a first color and each of the vertically-oriented stitches has a second color different than the first color.

In some embodiments, the plurality of attachment straps includes a first set of body-section loops coupled to the perimeter binding at each upper corner of the body section and a second set of body-section loops coupled to the perimeter binding and spaced inward from the first set of body-section loops.

In some embodiments, the sling further comprises a body-section adjustment system configured to change a width of the body section to raise and lower a patient's head.

In some embodiments, the body section has a first upper corner and a second upper corner and the adjustment system includes a first extensible-strap unit coupled to the perimeter binding and interconnecting the first outer corner of the body section and a first point on the perimeter binding between the first upper corner and the second upper corner and a second extensible-strap unit coupled to the perimeter binding and interconnecting the second outer corner of the body section and a second point on the perimeter binding between the first point and the second upper corner.

In some embodiments, the first and second extensible-strap units each include a first strap coupled to one of the first upper corner and the second upper corner, a second strap coupled to a corresponding one of the first point and the second point and a buckle coupled to the first strap and the second strap and configured to allow adjustment of at least one of the first strap and the second strap to raise and lower a head section of the sling body.

In some embodiments, the body section is formed to include a first cutout along a first lateral side of the body section and a second cutout along a second lateral side of the body section.

In some embodiments, an edge of the body section defining the first cutout and the second cutout is spaced apart from the perimeter binding to provide a first handle on the first lateral side and a second handle on the second lateral side.

In some embodiments, the first handle and the second handle are the only handles on the body portion.

In some embodiments, the sling body, the perimeter binding, and the plurality of attachment straps are all made from a material consisting of polyester.

In some embodiments, the sling further comprises an incontinence pad coupled removably to sling body by a plurality of adhesive strips that extend parallel with one another along a length of the sling body.

In some embodiments, the incontinence pad includes a first side flange and a second side flange on an opposite side of the incontinence pad as the first side flange and wherein the first and second side flanges are coupled to an underside of the sling body by an adhesive strip.

In some embodiments, the incontinence pad includes a at least one electrical trace fitted within the incontinence pad and a transponder tag coupled to the at least one electrical trace to provide a signal in response to moisture being present on the incontinence pad to notify a caregiver that an incontinence event has occurred.

In accordance with a fifth aspect of the present disclosure, a patient-lift sling includes a sling body configured to support a patient, a perimeter binding that extends around an outer edge of the sling body, a plurality of attachment straps coupled to the perimeter binding, and a body-section adjustment system configured to change a width of the body section to raise and lower a patient's head.

In some embodiments, the sling body has a first upper corner and a second upper corner and the adjustment system includes a first extensible-strap unit coupled to the perimeter binding and interconnecting the first outer corner of the sling body and a first point on the perimeter binding between the first upper corner and the second upper corner and a second extensible-strap unit coupled to the perimeter binding and interconnecting the second outer corner of the sling body and a second point on the perimeter binding between the first point and the second upper corner.

In some embodiments, the first and second extensible-strap units each include a first strap coupled to one of the first upper corner and the second upper corner, a second strap coupled to a corresponding one of the first point and the second point and a buckle coupled to the first strap and the second strap and configured to allow adjustment of at least one of the first strap and the second strap to raise and lower a head section of the sling body.

In some embodiments, the sling body includes at least one layer of warp-knit fabric that has a first stiffness value and the perimeter binding, the plurality of attachment straps, the first strap, and the second strap each include at least one layer of woven fabric that has a second stiffness value greater than the first stiffness value.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Although this disclosure refers to specific embodiments, it will be understood by those skilled in the art that various changes in form and detail may be made without departing from the subject matter set forth in the accompanying claims.

Figure 1:
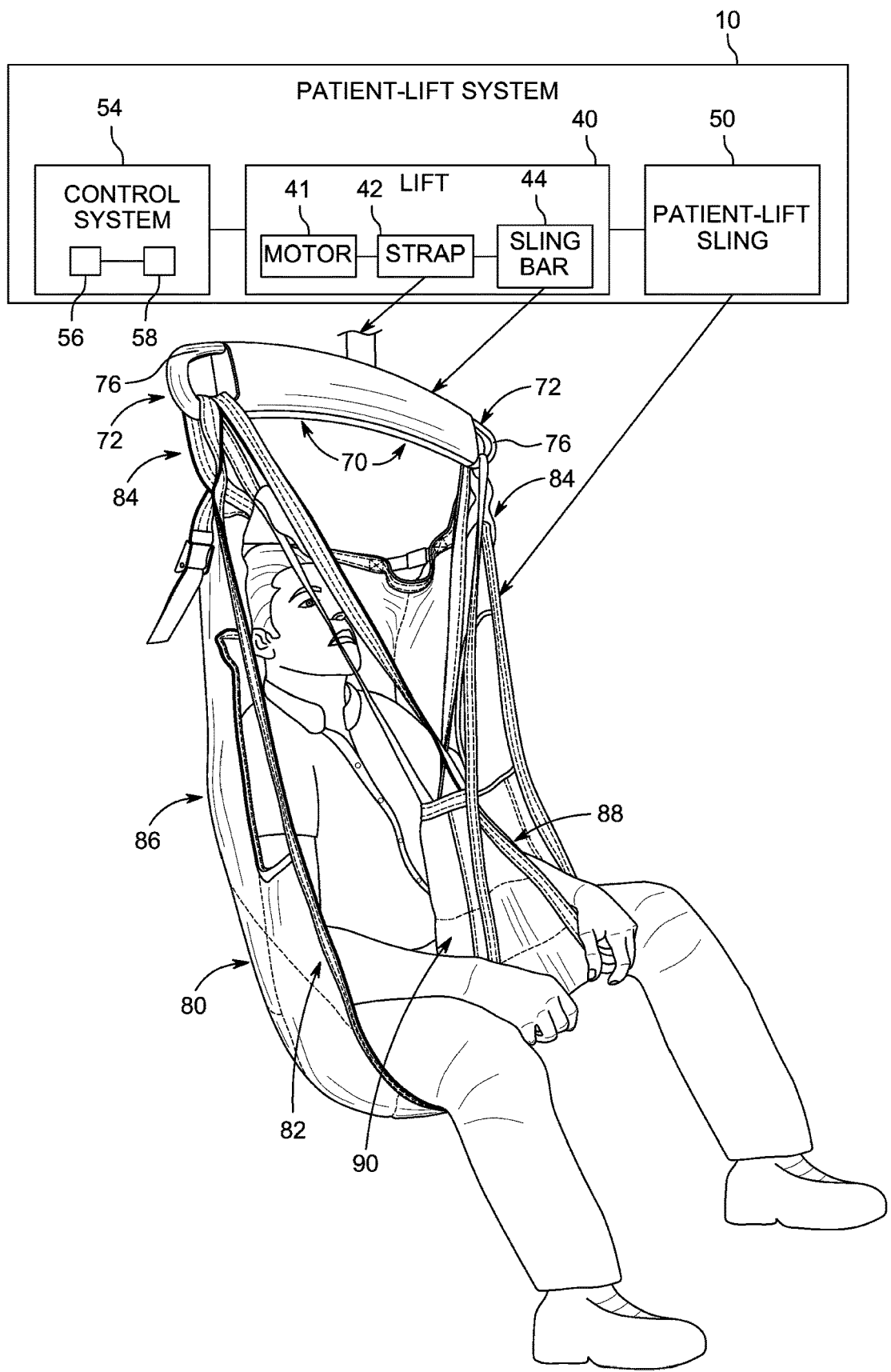
FIG. 1 is a perspective view of an overhead patient lift system, in accordance with the present disclosure, showing the patient lift system including a lift, a patient-lift sling holding a patient above ground from a sling bar, and a control system configured to control movement of the lift to raise and lower the patient in the patient-lift sling.

A patient lift system 10, according to one contemplated embodiment, is configured as an overhead patient lift system as shown in FIG. 1. The lift system 10 of FIG. 1 may be coupled to a ceiling of a room, a mobile patient lift system (e.g., a powered sit-to-stand lift or stand assist lift), or another person lifting device (not shown) and configured to raise and lower a patient-lift sling 50 and a patient being supported by the patient-lift sling 50. In some contemplated embodiments, portions of the lift system 10 are constructed as disclosed in U.S. Patent Application Publication No. 2012/0000876A1, which is hereby incorporated herein by reference in its entirety to the extent not inconsistent with the present disclosure which shall control as to any inconsistencies.

The lift system 10 includes, a lift 40, the patient-lift sling 50, and a control system 54 as shown in FIG. 1. The lift 40 includes a motor 41, a strap 42 configured to be extended and retracted by the motor 41, and a sling bar 44 coupled to a lower end of the strap 42 by a coupler such as a pin, latch, or hook. The motor 41 may be arranged in a housing and is configured to raise and lower the strap 42 by, for example, winding and unwinding the strap 42 on a drum (not shown). As the strap 42 is wound or unwound, the sling bar 44 and the sling 50 attached thereto is raised and lowered. The control system 54 includes a microprocessor 56 and a memory storage device 58 storing instructions that when executed by the microprocessor 56 control up and down movement of the sling bar 44 in response to user inputs into a control panel or a pendant control device coupled to the lift 40.

The sling bar 44 is coupled to the end of the strap 42 and includes arms 70 with sling attachment hooks 72 at the ends of the arms 70. The sling attachment hooks 72 are configured to receive and removably retain straps 84 of the sling 50. The sling attachment hooks 72 include a retaining element 76 that is configured to prevent the sling 50 from disengaging the attachment hooks 72. The retaining element 76 includes a spring loaded bail, finger, rod, post, or the like that is normally held in a closed position under the spring bias but that is movable to an open position during attachment of the loops of the sling 50 onto the respective hook 72. In use, the retaining elements 76 prevent the loops of the sling 50 from inadvertently moving off of the respective hooks 72. The sling 50 is used to comfortably support a person being transported by the lift system 10.

Figure 2:
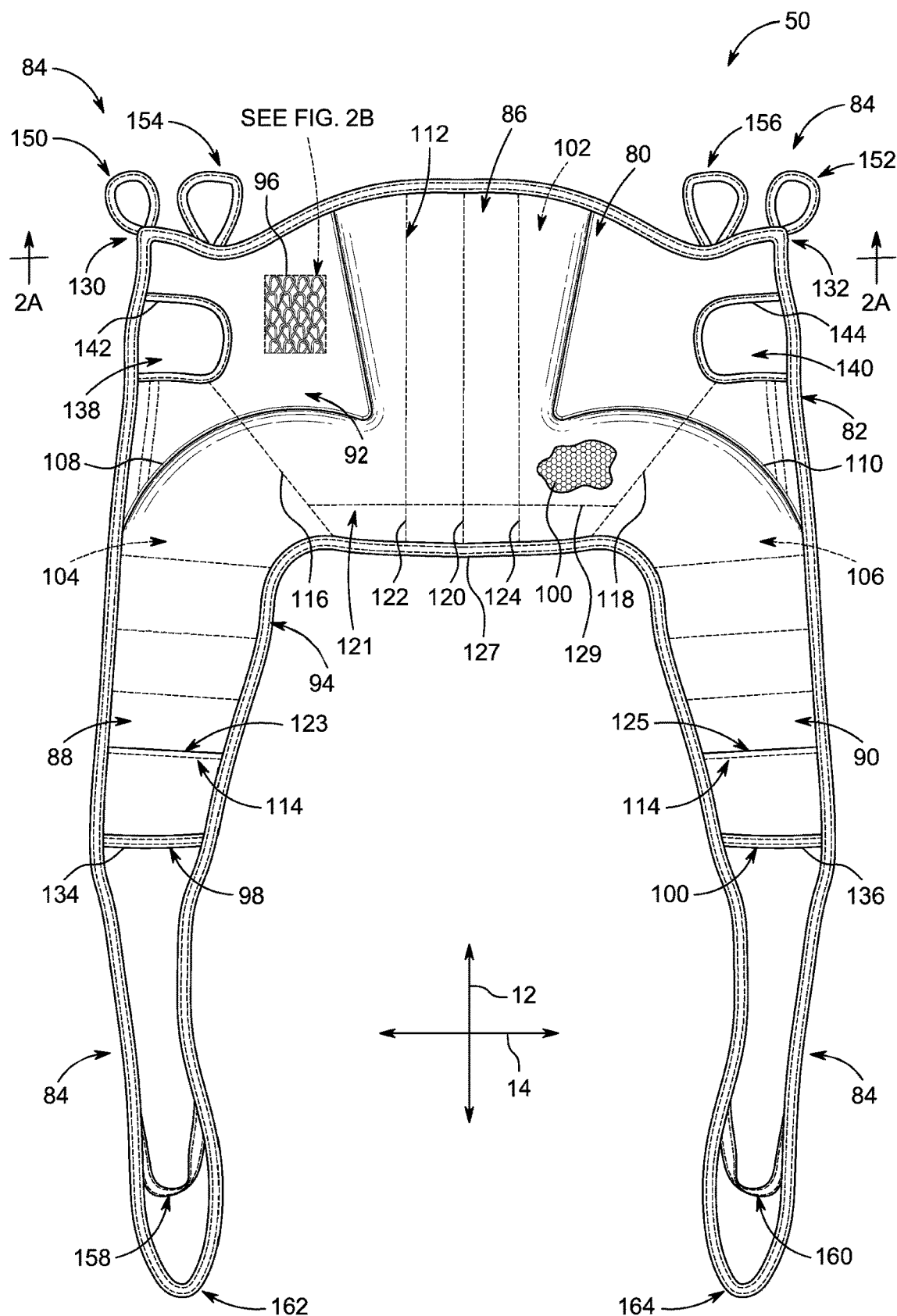
FIG. 2 is a top plan view of the patient-lift sling of FIG. 1 showing the sling having a sling body including a body section and a pair of leg sections extending downwardly from the body section, a perimeter binding coupled to an outer edge of the sling body, and a plurality of attachment straps coupled to the perimeter binding.
Figure 2A:
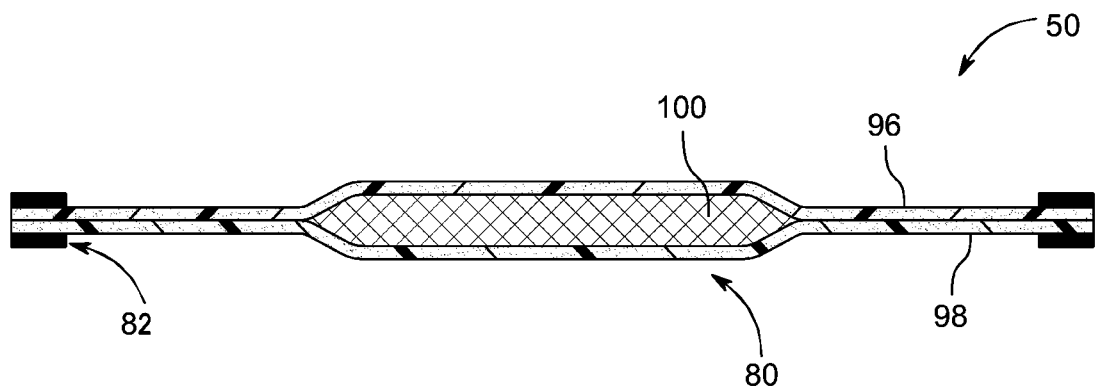
FIG. 2A is a cross sectional view taken along line 2A-2A in FIG. 2 showing that the sling body includes a first layer of warp-knit fabric, a second layer of warp-knit fabric, and an inner layer of spacer material between the first layer and the second layer.

The patient-lift sling 50 includes a sling body 80, a perimeter binding 82, and a plurality of attachment straps 84 as shown in FIGS. 1 and 2. The sling body 80 is configured to comfortably seat a patient being transported by the lift assembly 22. The perimeter binding 82 is coupled to an outer perimeter of the sling body 80 to reinforce the patient-lift sling 50 to bear the weight of the patient. The plurality of attachment straps 84 are coupled to the perimeter binding 82 and attach to the sling attachment hooks 72 to retain the patient-lift sling 50 to the sling bar 44 or another suitable lifting apparatus.

The sling body 80 includes a main body section 86, a first leg section 88, and a second leg section 90 as shown in FIGS. 1 and 2. The main body section 86 is configured to engage and support an upper body of the patient as shown in FIG. 1. The first leg section 88 and the second leg section 90 wrap beneath the left and right legs of the patient, respectively. The first leg section 88 and the second leg section 90 crisscross in front of the patient and attach to opposite sides of the sling bar 44 by corresponding attachment straps 84 such that the patient is held by the patient-lift sling 50 beneath the patient's legs and in a seated and slightly reclined position.

The sling body 80 is made from a highly-stretchable fabric that increases comfort for the patient. The perimeter binding 82 and the plurality of attachment straps 84 are made from a fabric that is less stretchable than the fabric of the sling body 80 to support and reinforce the patient-lift sling 50 to hang from the sling bar 44 above ground. In some embodiments, the sling body 80, the perimeter binding 82, and the attachment straps 84 are all made from a material consisting of polyester.

The sling body 80 includes at least one layer of fabric 92 that has a first stiffness value while the perimeter binding 82 and each of the attachment straps 84 include at least one layer of fabric 94 that has a second stiffness value greater than the first stiffness value. The at least one layer of fabric 92 included in the sling body 80 is a warp-knit fabric while the at least one layer of fabric 94 in the perimeter binding 82 and the plurality of attachment straps 84 is a woven fabric. The warp-knit fabric 92 of the sling body 80 provides greater flexibility than the woven fabric 94 of the perimeter binding 82 and the plurality of attachment straps 94. In the illustrative embodiment, the fabric 92 of the sling body 80 and the fabric 94 of the perimeter binding 82 and the plurality of attachment straps 94 are both constructed from one or more fiber strands made from polyester. In other embodiments, the fabrics 92, 94 may be made from a different material compared to one another.

Figure 2B:
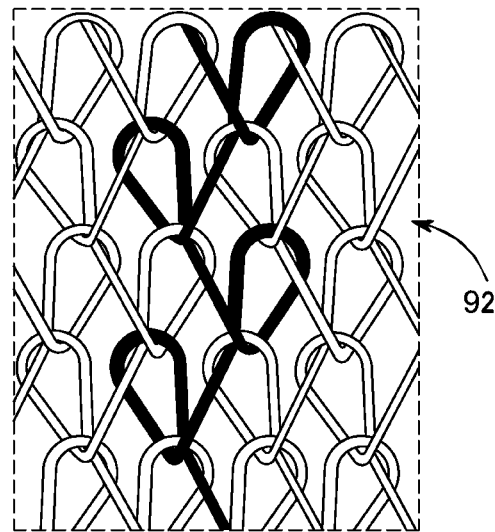
FIG. 2B is an enlarged portion of FIG. 2 showing how the first layer and the second layer are warp-knitted to provide a highly stretchable fabric.

The fabric 92 of the sling body 80 has one or more continuous strands of fiber that are warp knitted together as suggested in FIG. 2B. Each strand of fiber zig-zags laterally and interlocks or weaves with each neighboring row to form the warp-knit pattern shown in FIG. 2B. One of the strands of fibers of fabric 92 has been highlighted in FIG. 2B to show this zig-zag, warp-knit pattern. The warp-knit pattern of fabric 92 allows the fabric to stretch in all directions compared to other woven fabrics that only allow stretch in a diagonal direction to each of the fibers. Other types of warp-knit patterns are also possible.

The warp knit fabric 92 allows for greater stretch compared to a woven fabric such as the fabric 94 included in the perimeter binding 82, the plurality of attachment straps 84, and other slings. In one example, the warp-knit fabric 92 is referred to as highly-stretchable because it has a percent elongation of about 5% in the width direction to about 15% in the length (or warp) direction according to the BSI-BS 4952 test standard in effect at the time of filing of the present application. In another example, the warp-knit fabric 92 is referred to as highly-stretchable because it has a percent elongation of about 50% to about 90% in the width (or weft) direction and a percent elongation of about 50% to about 90% in the length direction according to the BSI-BS 2576 test standard in effect at the time of filing of the present application.

The warp-knit fabric 92 has a relatively low basis weight which contributes to the low stiffness of the fabric 92. In some embodiments, the fabric 92 included in the sling body 80 has a basis weight within a range of about 300 $g/m^2$ to about 450 $g/m^2$. In some embodiments, the fabric 92 included in the sling body 80 has a basis weight within a range of about 380 $g/m^2$ to about 420 $g/m^2$. In some embodiments, the basis weight of the fabric 92 included in the sling body 80 is less than 380 $g/m^2$. In one example, the basis weight of the fabric 92 included in the sling body 80 is about 315 g/m². In another example, the basis weight of the fabric 92 included in the sling body 80 is less than 315 g/m².

The warp-knit fabric 92 has a lower tensile strength compared to the woven fiber 94 but is still able to support a patient while increasing comfort for the patient by contributing to the low stiffness of the fabric 92. In some embodiments, the fabric 92 included in the sling body 80 has a tensile strength within a range of about 1300 Newtons (N) to about 1700 N in the length direction of the fabric 92 according to the BSI-BS 2576 test standard in effect at the time of filing of the present application. In some embodiments, the fabric 92 included in the sling body 80 has a tensile strength of at least 690 N in the length direction according to the BS EN ISO 13934-1 strip method test standard in effect at the time of filing of the present application. In some embodiments, the fabric 92 included in the sling body 80 has a tensile strength of at least 1300 N in the width direction according to the BSI-BS 2576 test standard in effect at the time of filing of the present application. In some embodiments, the fabric 92 included in the sling body 80 has a tensile strength of at least 1680 N in the width direction according to the BS EN ISO 13934-1 strip method test standard in effect at the time of filing of the present application. Other types of woven fabrics such as fabric 94 included in the perimeter binding 82 and the plurality of attachment straps 84 may have a tensile strength that is higher than the tensile strength of the fabric 92 included in the sling body 80. However, woven fabrics such as fabric 94 are not highly stretchable, and instead are used to reinforce the patient-lift sling 50 for attachment on the sling bar 44.

Other factors may also contribute to the lower stiffness of the sling body 80 compared to the perimeter binding 82, the plurality of attachment straps 84, and other slings that don't include a highly stretchable fabric like fabric 92. A number of threads per unit of fabric 92 of the sling body 80 is lower than the number of threads per unit of fabric 94. In one example, a number of courses in the fabric 92 is within a range of about 20 per inch and about 35 per inch. In another example, a number of courses in the fabric 92 is within a range of about 29 per inch and about 35 per inch. In another example, a number of courses in the fabric 92 is about 22 per inch. In another example, a number of courses in the fabric 92 is about 32 per inch. In one example, a number of wales in the fabric 92 is within a range of about 17 per inch and about 21 per inch. In another example, a number of wales in the fabric 92 is within a range of about 19 per inch and about 21 per inch. In another example, a number of wales in the fabric 92 is about 17 per inch. In another example, a number of wales in the fabric 92 is about 20 per inch. Other slings have been made from a fabric with about 70 courses per inch and about 46 wales per inch which provides a higher stiffness. The one or more strands of fiber forming the sling body 80 may also have a smaller thickness than the one or more strands of fiber forming the perimeter binding 82, the plurality of attachment straps 84, and other slings to provide a lower stiffness.

Figure 3:
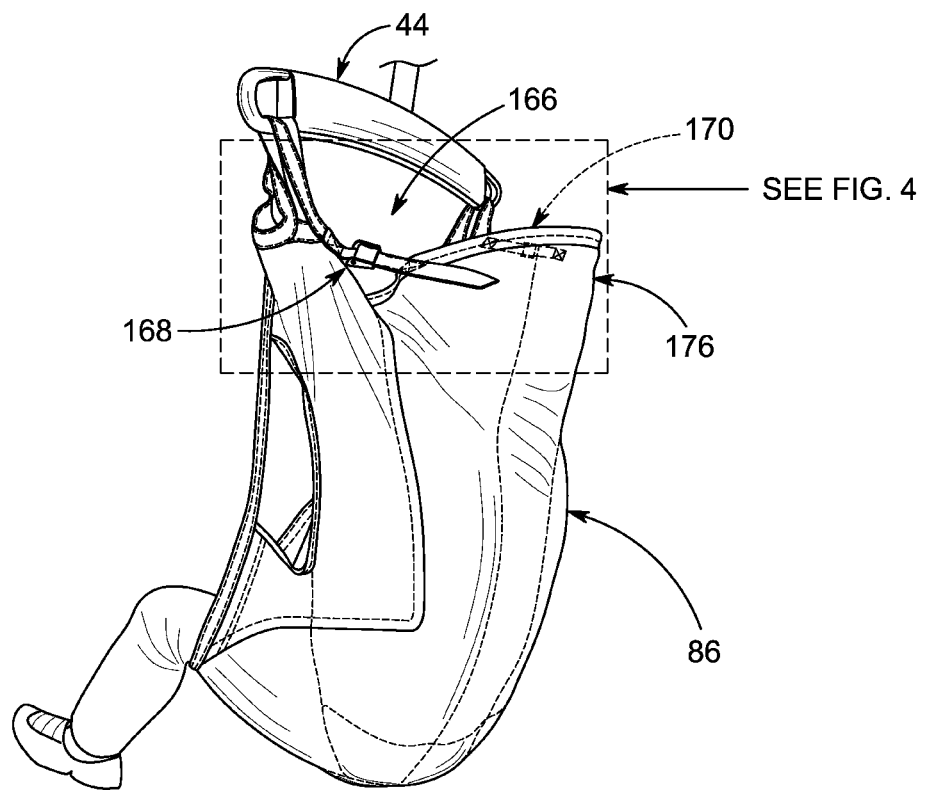
FIG. 3 is a perspective view of a back side of the patient-lift sling.

In the illustrative embodiment, the sling body 80 includes a first layer of warp-knit fabric 96, a second layer of warp-knit fabric 98, and an inner layer 100 of spacer material as shown in FIGS. 2 and 3. The first layer of warp-knit fabric 96 defines a back side of the sling body 80 and faces away from the patient. The second layer of warp-knit fabric 98 defines a front side of the sling body 80 and faces toward the patient. The inner layer 100 is arranged to lie between the first and second layers 96, 98 and is configured to provide cushioning for the patient. The spacer material forming the inner layer 100 is a three-dimensional mesh that allows air and moisture to pass therethrough and has a thickness that is greater than both the first and second layers 96, 98. The spacer material of inner layer 100 is sewn or otherwise attached to the perimeter binding 82 to reinforce the sling body 80 so that uncomfortable, rigid laths (not shown), sometimes included in some slings, are omitted from the patient-lift sling 50.

The inner layer 100 of the spacer material is arranged between the first and second layers 96, 98 in areas of the sling body 80 that are most likely to come into contact with the patient so as to maximize comfort for the patient. A portion of the inner layer 100 is shown in FIG. 2 through a cutaway through second layer 98. The inner layer 100 of the spacer material includes an upper-body portion 102 located in the body section 86, a first leg portion 104 coupled with the upper-body portion 102 and located in the first leg section 88, and a second leg portion 106 coupled with the upper-body portion 102 and located in the second leg section 90 as shown in FIG. 2. The upper-body portion 102 corresponds with the patient's back, shoulders, and head and tapers outwardly to increase in width as the upper-body portion extends away from the leg portions 104, 106. The first and second leg portions 104, 106 correspond with the patient's hips, glutes and thighs and are shaped with a curved upper edge 108, 110 to conform to the patient's hips, glutes, and thighs when the first and second leg sections 88, 90 are crisscrossed and attached to respective hooks 72 to support a patient above ground.

The first layer 96, the second layer 98 and the inner layer 100 are integrated together by a plurality of stitches included in the sling body 80 as shown in FIG. 2. The plurality of stitches are located and oriented relative to one another to maximize flexibility of the sling body 80. The plurality of stitches includes a plurality of vertically-oriented stitches 112 located on the body section 86, a plurality of horizontally-oriented stitches 114 located on the first and second leg sections 88, 90, and a pair of diagonally-oriented stitches 116, 118. One of the diagonally-oriented stitches 116 is located between the plurality of vertically-oriented stitches 112 and the first leg section 88. The other of the diagonally-oriented stitches 118 is located between the vertically-oriented stitches 112 and the second leg section 90. The location and orientation of each of the stitches 112, 114, 116, 118 maximizes stretchability of the sling body 80 by orienting each of the stitches 112, 114, 116, 118 to allow the sling body 80 to conform to the patient's body when the leg sections 88, 90 are crisscrossed and supporting a patient above ground. With the stitches 112, 114, 116, 118 in these positions and orientations, the first and second layers of warp-knit fabric 96, 98 can stretch at or near their full potential without being obstructed by any of the stitches 112, 114, 116, 118.

The vertically-oriented stitches 112 may be used as visual guides to facilitate positioning a patient on the patient-lift sling 50. The vertically-oriented stitches 112 are spaced apart from one another and located such that a first vertical stitch 120 is substantially in a central location on the sling body 80 to align with a patient's spine when the patient is laid on the sling 50. The vertically-oriented stitches 112 further include a second vertical stitch 122 spaced apart from the first vertical stich 120 and a third vertical stitch 124 spaced apart from the first vertical stitch 120 opposite the second vertical stitch 122. The second vertical stich 122 may be configured to align with the patient's left shoulder blade and the third vertical stitch 124 may be configured to align with the patient's right shoulder blade. Alternatively, the second and third vertical stitches 122, 124 may be used as visual guides relative to the patient's shoulders or another symmetrical body characteristic of the patient to properly position the patient on the sling 50. In some embodiments, the sling body 80 has a first color and each of the vertically-oriented stitches 112 has a second color different than the first color so that the vertically-oriented stitches 112 are distinguishable from the sling body 80 to use in positioning the patient on the sling 50.

The sling 50 further includes a central pocket layer 121 coupled to the body section 86, a first side pocket layer 123 coupled to the first leg section 88, and a second pocket layer 125 coupled to the second leg section 90 as shown in FIG. 2. Each of the pockets 121, 123, 125 are arranged to lie on the back side of the sling 50 to aid in positioning the sling 50 on a patient. The central pocket layer 121 is made from the same warp-knit fabric as fabric 92 and is located adjacent to a lowermost edge 127 of the body section 86. The central pocket layer 121 has an opening 129 that faces upwardly away from the lowermost edge 127 for access between the central pocket layer 121 and the first layer 96 so that a caregiver can maneuver the sling 50 around the patient's torso, hips and glutes. The vertically-oriented stitches 112 may divide the central pocket 121 into multiple pockets to reduce stretchability of the central pocket layer 121 for better control in maneuvering the sling 50 around the patient. The first and second side pocket layers 123, 125 open upwardly away from ends 134, 136 of the leg sections 88, 90 for access between the first layer 96 and the side pocket layers 123, 125 to maneuver the leg sections 88, 90 around the patient's legs. The first and second side pocket layers 123, 125 are made from a different fabric with a lower coefficient of friction than the first and second layers 96, 98 and the central pocket layer 121 so that the leg sections 88, 90 can slide along surfaces as the leg sections are maneuvered around the patient's legs.

The perimeter binding 82 extends around an outer perimeter edge of the sling body 80 and is sewn or attached to the sling body 80 to integrate the perimeter binding 82 and the sling body 80 together as shown in FIG. 2. The sling body 80 distributes the weight of the patient to the perimeter binding 82 and then to the attachment straps 84. As such, the perimeter binding 82 and the attachment straps 84 cooperate to reinforce the sling 50 to hold the weight of the patient. In some embodiments, the perimeter binding 82 is made integrally with all or some of the plurality of attachment straps 84 such that the perimeter binding 82 and the attachment straps 84 form a continuous unit of material that extends around the perimeter of the sling body 80. The perimeter binding 82 forms the plurality of attachment straps 84 at corners 130, 132, of the body section 86 and ends 134, 136 of the first and second leg sections 88, 90.

The body section 86 is formed to include a lateral cutout 138, 140 on each side of the body section 86 as shown in FIG. 2. The cutouts 138, 140 open outwardly away from the body section 86 and cutout portions 142, 144 of the perimeter binding 82 line an edge of each cutout 138, 140. The perimeter binding also extends across the cutouts 138, 140 to be spaced apart from the cutout portions 142, 144 and provide handles that can be used by the patient or the caregiver for support or to maneuver the sling 50.

Some of the plurality of attachment straps 84 may be sewn or attached to the perimeter binding 82 or to each other to provide multiple attachment straps 84 at each corner 130, 132 and end 134, 136. The sling 50 includes a first set of body-section loops 150, 152 coupled to the perimeter binding at corners 130, 132 of the body section 86, a second set of body-section loops 154, 156 coupled to the perimeter binding at corners 130, 132 of the body section 86. The second set of body-section loops 150, 152 are spaced inwardly from the first set of body-section loops 150, 152. The sling 50 can be adjusted to fit larger or smaller patients by using either the first set of body-section loops 150, 152 or the second set of body-section loops 154, 156. The first set of body-section loops 150, 152 are also called outer loops and may be coupled to respective hooks 72 of the lift 40 to accommodate a relatively larger patient. The second set of body-section loops 154, 156 are also called inner loops and may be coupled to respective hooks 72 of the lift 40 to accommodate a relatively smaller patient. An effective width of the sling 50 is smaller when the inner loops 154, 156 are used compared to when the outer loops 150, 152 are used. The inner and outer loops 150, 152, 154, 156 may all be coupled to each respective hook 72 of the lift 40 to block portions of the sling 50 from moving or flapping The sling 50 also includes a first set of leg-section loops 158, 160 and a second set of leg-section loops 162, 164 as shown in FIG. 2. The leg-section loops shown in FIG. 2 are similar to the loops shown and described in U.S. Pat. No. 9,433,548, issued on Sep. 6, 2016, which is expressly incorporated by reference herein in its entirety for the purpose of describing leg section loops. The first set of leg-section loops 158, 160 are spaced inwardly from the second set of leg-section loops 162, 164. The first set of leg-section loops 158, 160 may be coupled to respective hooks 72 of lift 40 to accommodate a relatively smaller patient in sling 50. The second set of leg-section loops 162, 164 may be coupled to respective hooks 72 of lift 40 to accommodate a relatively larger patient. An effective length of the sling 50 is smaller when the first set of leg-section loops 158, 160 are used compared to when the second set of leg-section loops 162, 164 are used. Accordingly, sling 50 is adjustable in both width 12 and length 14 directions to fit patients of different sizes.

Figure 4:
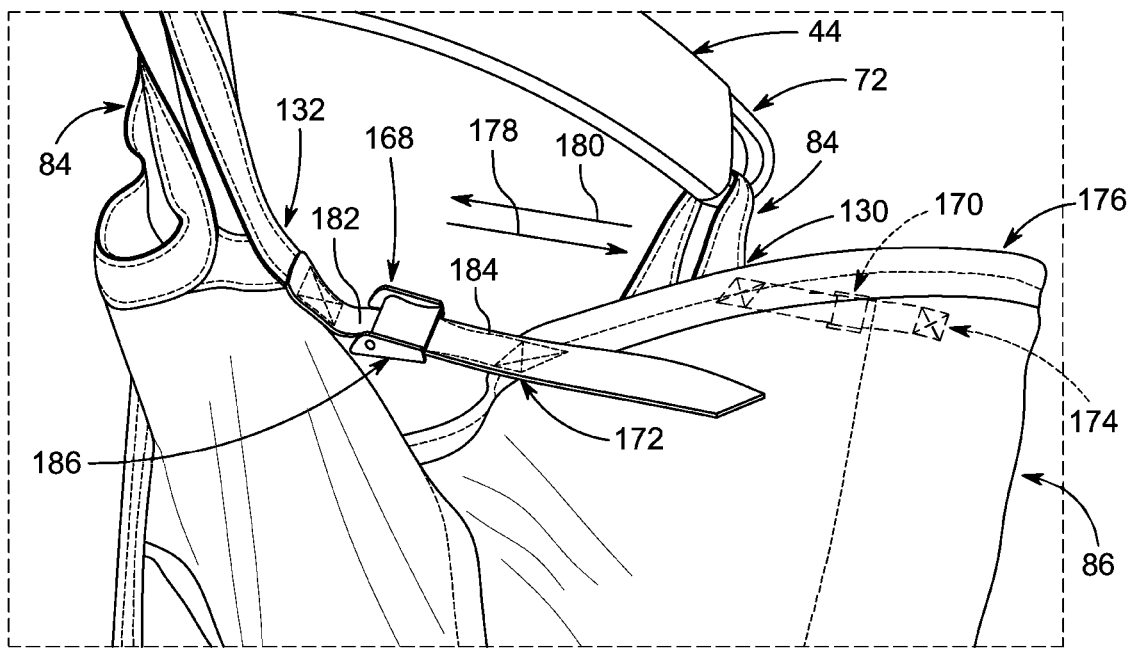
FIG. 4 is an enlarged portion of FIG. 3 showing a portion of an adjustment system that provides a better fit for occupants of different sizes.

The sling 50 may further include a body-section adjustment system 166 that is configured to change a width of the body section 86 and raise and lower a patient's head when the sling 50 is hanging from lift 40 as suggested in FIGS. 3 and 4. The body-section adjustment system 166 includes a first extensible-strap unit 168 on a first side of the sling 50 and a second extensible-strap unit 170 on an opposite second side of the sling 50. The first extensible strap unit 168 is coupled to the perimeter binding 82 and interconnects a first corner 132 of the body section 86 and a first point 172 on the perimeter binding between the first corner 132 and a second corner 130. The second extensible-strap unit 170 is coupled to the perimeter binding 82 and interconnects the second corner 130 of the body section 86 and a second point 174 on the perimeter binding 82 between the first point 172 and the second upper corner 130. Each extensible-strap unit 168, 170 is adjustable to extend and retract the first point 172 and the second point 174 toward and away from their respective corner 130, 132 thereby moving a head section 176 of the body section 86 toward and away from corners 130, 132 as indicated by arrows 178, 180 in FIG. 4.

Each extensible-strap unit 168, 170 is identical, so only the first extensible strap unit 168 is discussed below and this disclosure is incorporated by reference for the second extensible-strap unit 170. The extensible-strap unit 168 includes a first strap 182, a second strap 184 spaced apart from the first strap 182 and a buckle 186 coupled to the first strap 182 and the second strap 184 as shown in FIG. 4. The first strap 182 is fixed to corner 132 and engages releasably with the buckle 186. The second strap 184 is fixed to the first point 172 and the buckle 186 is fixed to the second strap opposite the first point 174. The first strap 182 is threaded through the buckle 186 and may be adjusted to extend or retract the first point 172 toward and away from the corner 132. The buckle 186 is configured to lock the first strap 182 in position relative to the first point 172 to block further adjustment of the strap 182 until the buckle is released from the strap 182.

Figure 5:
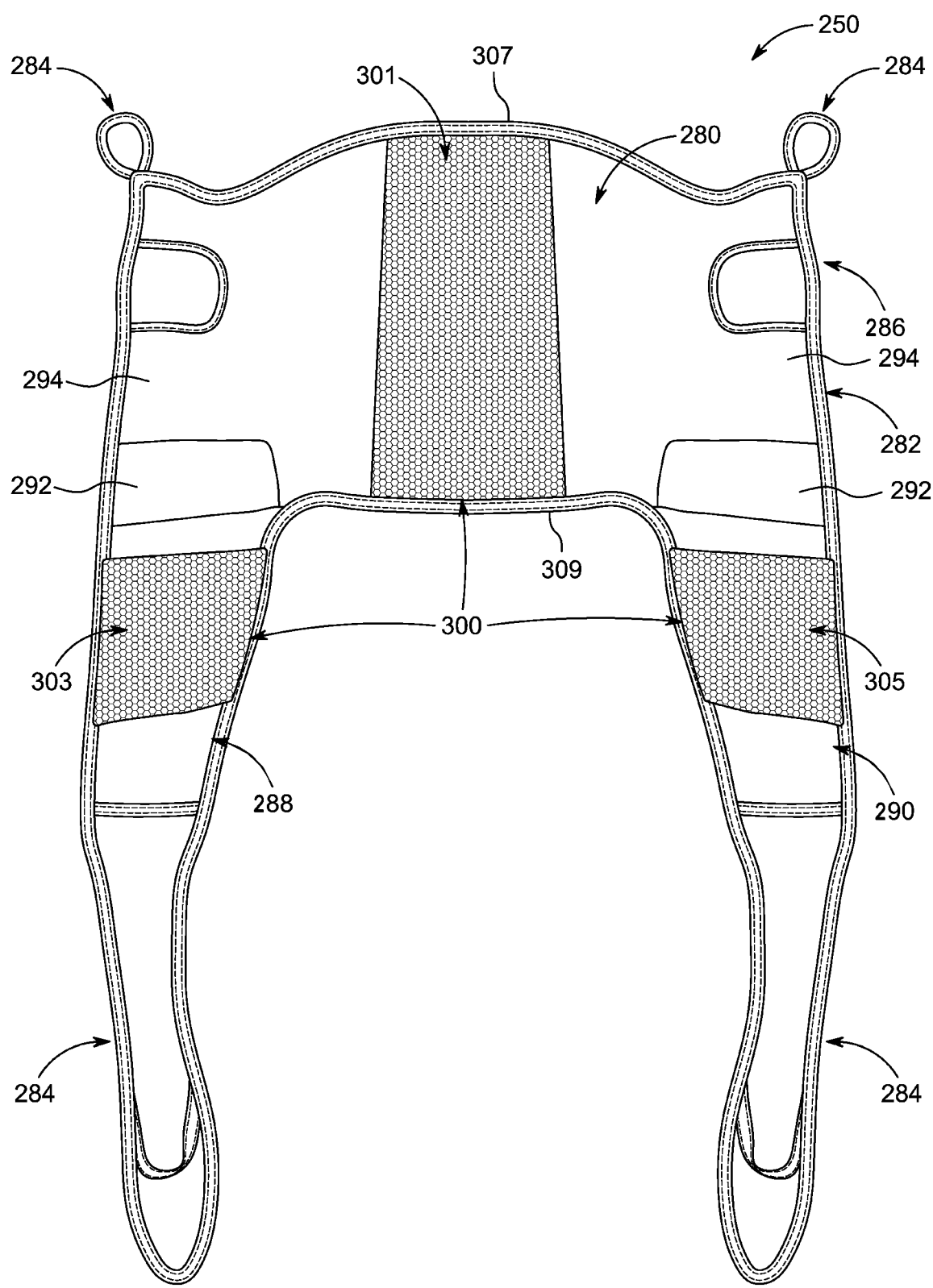
FIG. 5 is a top plan view of another embodiment of a patient-lift sling, in accordance with the present disclosure.

A second embodiment of a patient-lift sling 250 is shown in FIG. 5. Patient-lift sling 250 is similar to patient-lift sling 50. Accordingly, similar reference numbers in the 200 series are used to indicate similar features between sling 50 and sling 250. The disclosure of sling 50 is hereby incorporated by reference herein for sling 250 except for the differences described below. All of the features described for both slings 50, 250 may be included in either sling 50 or sling 250.

The sling 250 includes a sling body 280, a perimeter binding 282, and a plurality of attachment straps 284. The sling body 280 includes a body section 286 and first and second leg sections 288, 290. The sling body 280 is made from at least one layer of fabrics 292, 294 that are sewn or attached together to form the sling body 280. Fabric 292 is warp-knitted like fabric 92 to be highly flexible while fabric 294 is woven to have a stiffness that is greater than fabric 292. The sling body 280 is constructed such that fabric 292 forms a first interface portion located between the body section 286 and the first leg section 288 and forms a second interface portion located between the body section 286 and the second leg section 290. The fabric 292 is positioned in areas that deform when the leg sections 288, 290 are crisscrossed around the patient's legs to increase comfort for the patient.

The sling body 280 may further include a layer of spacer material 300 as shown in FIG. 5. The spacer material 300 may be selectively positioned in various locations where the patient is most likely to come into contact with the sling 250. The spacer material may include a first patch 301 located on the body section 286, a second patch 303 located on the first leg section 288, and a third patch located on the second leg section 290. The first patch 301 extends from an uppermost edge 307 of the body section 286 to a lowermost edge 309 of the body section 286 and is sewn together with the perimeter binding 282. The second patch 303 extends only partway along the first leg section 288 on portions of the first leg section 288 that contact the patient's right leg while being supported by the sling 250. The third patch 305 extends only partway along the second leg section 290 on portions of the second leg section 290 that contact the patient's left leg while being supported by the sling 250. The second and third patches 303, 305 are spaced apart from the first patch 301.

A third embodiment of a patient-lift sling 450 is shown in FIGS. 6-9. The sling 450 includes a sling body 480, a perimeter binding 482, and a plurality of attachment straps 484. The sling 450 is arranged to be straddled by a patient to assist the patient in standing. The sling body 480 is made from a fabric material such as fabric 92 or fabric 94 described above. The perimeter binding 482 is sewn or attached around a perimeter edge of the sling body 480. The plurality of attachment straps 484 are integral with or otherwise coupled to the perimeter binding 482. The sling body 480 distributes the weight of the patient to the perimeter binding 482 while the perimeter binding 482 and the attachment straps 484 reinforce the sling 450 to bear the weight of the patient. The sling body 480 may be made from a highly-stretchable fabric like fabric 92.

Figure 6:
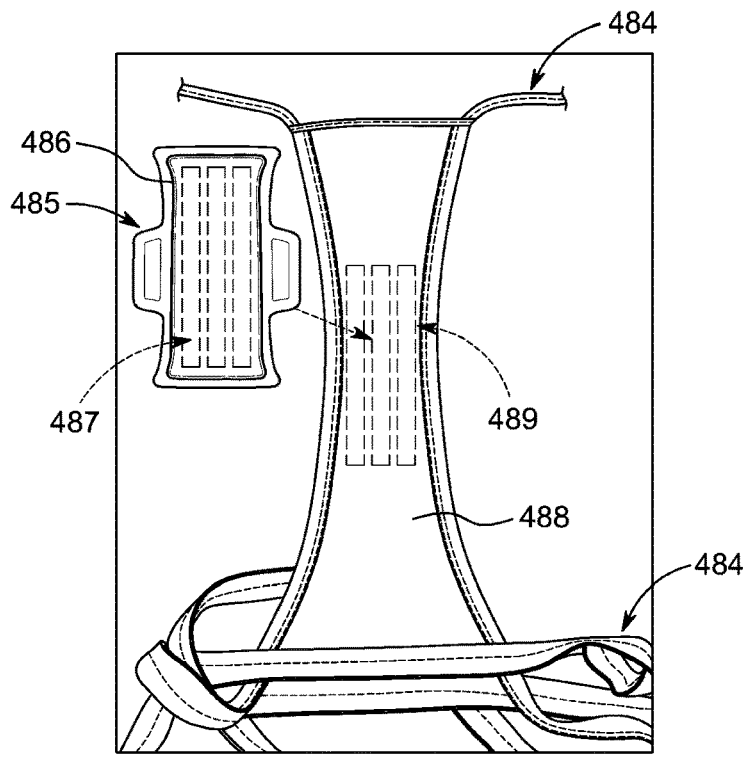
FIG. 6 is a top perspective view of another embodiment of a patient-lift sling including a disposable incontinence pad.
Figure 7:
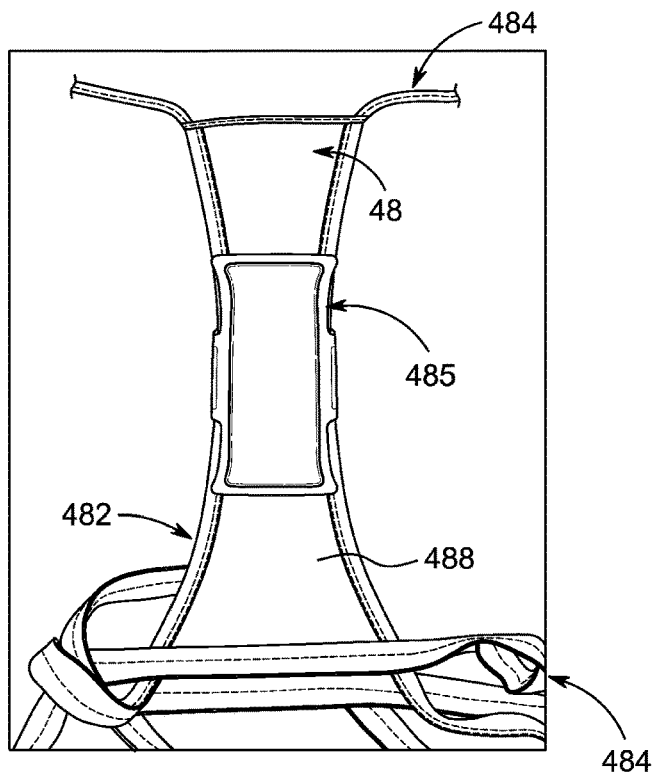
FIG. 7 is a top perspective view of the patient-lift sling with the disposable incontinence pad attached to a body section of the patient-lift sling.

The sling 450 further includes a disposable incontinence pad 485 that is configured to be removably coupled to the sling body 480 and/or the perimeter binding 482, as shown in FIGS. 6 and 7, to absorb fluids so that the sling 450 does not need to be washed after each use. The incontinence pad 485 is attached removably to the sling body 480 using a plurality of adhesive patches 487, 489 coupled to a bottom surface 486 of the incontinence pad 485 and an top surface 488 of the sling body 480. The adhesive patches 487, 489 are arranged as parallel strips between the incontinence pad 485 and the sling body 480 but may be arranged at any orientation in other embodiments. The incontinence pad 485 has a shape to conform to sling body 480 and/or the perimeter binding 482 to cover the top surface 488 of the sling body 480. The incontinence pad 454 flares outwardly at each end 498, 499

Figure 8:
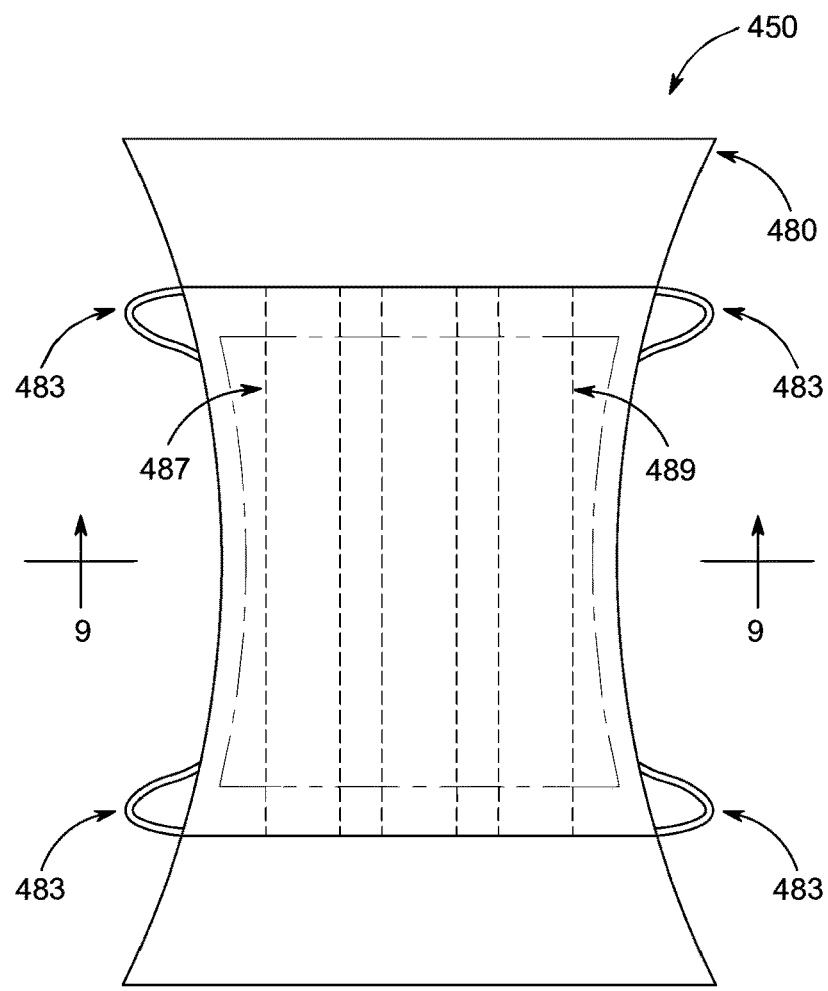
FIG. 8 is a top plan view of a portion of the patient-lift sling from FIG. 7 showing the incontinence pad.

In the illustrative embodiment, the adhesive patches 487, 489 are hook-and-loop structures that mesh when brought into contact with one another to retain the incontinence pad 485 in place on the sling body 480. In other embodiments, another suitable adhesive or structure may be used to retain the incontinence pad 485 on the sling body 480. For example, the incontinence pad 485 may include straps 483 that wrap around the sling body 480 such that the incontinence pad slides on the sling body 480 as shown in FIG. 8. The straps 483 may be used alone or with the adhesive patches 487, 489.

Figure 9:
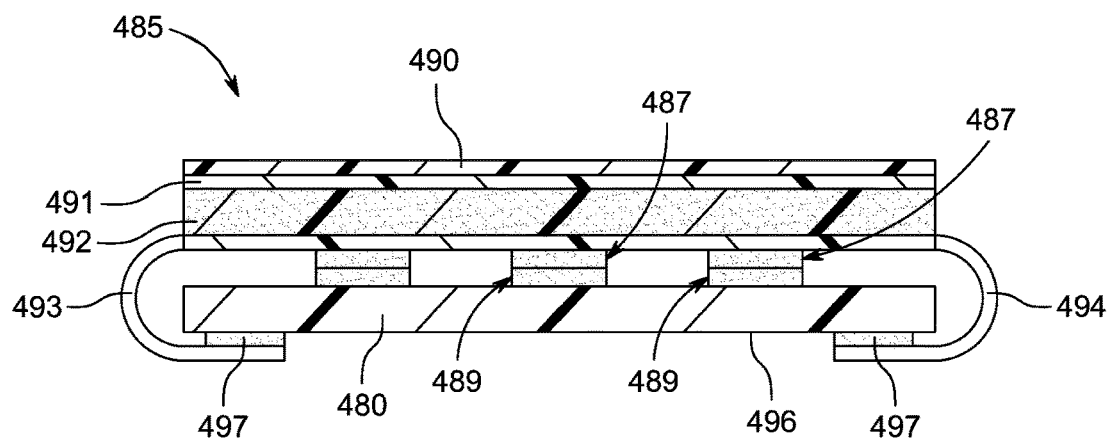
FIG. 9 is a sectional view of the patient-lift sling taken along line 9-9 in FIG. 8.

The incontinence pad 485 includes a top layer 490, an optional acquisition distribution layer 491, an absorbent core 492, and a backing layer 493 as shown in FIG. 9. The top layer 490 is fluid permeable and retains the acquisition distribution layer 491 and the absorbent core 492 to the backing layer 493. The acquisition distribution layer 491 is configured to distribute any fluid collected through the top layer 490 evenly into the absorbent core 492. The absorbent core retains the fluid collected. The backing layer 493 is fluid impermeable to block any fluid from being transferred to the sling body 480 from the absorbent core 492. The backing layer 493 may include multiple layers, such as a fluid impermeable film layer, a non-woven reinforcement layer, and an adhesive layer to bind the fluid impermeable film layer to the non-woven reinforcement layer.

Figure 10:
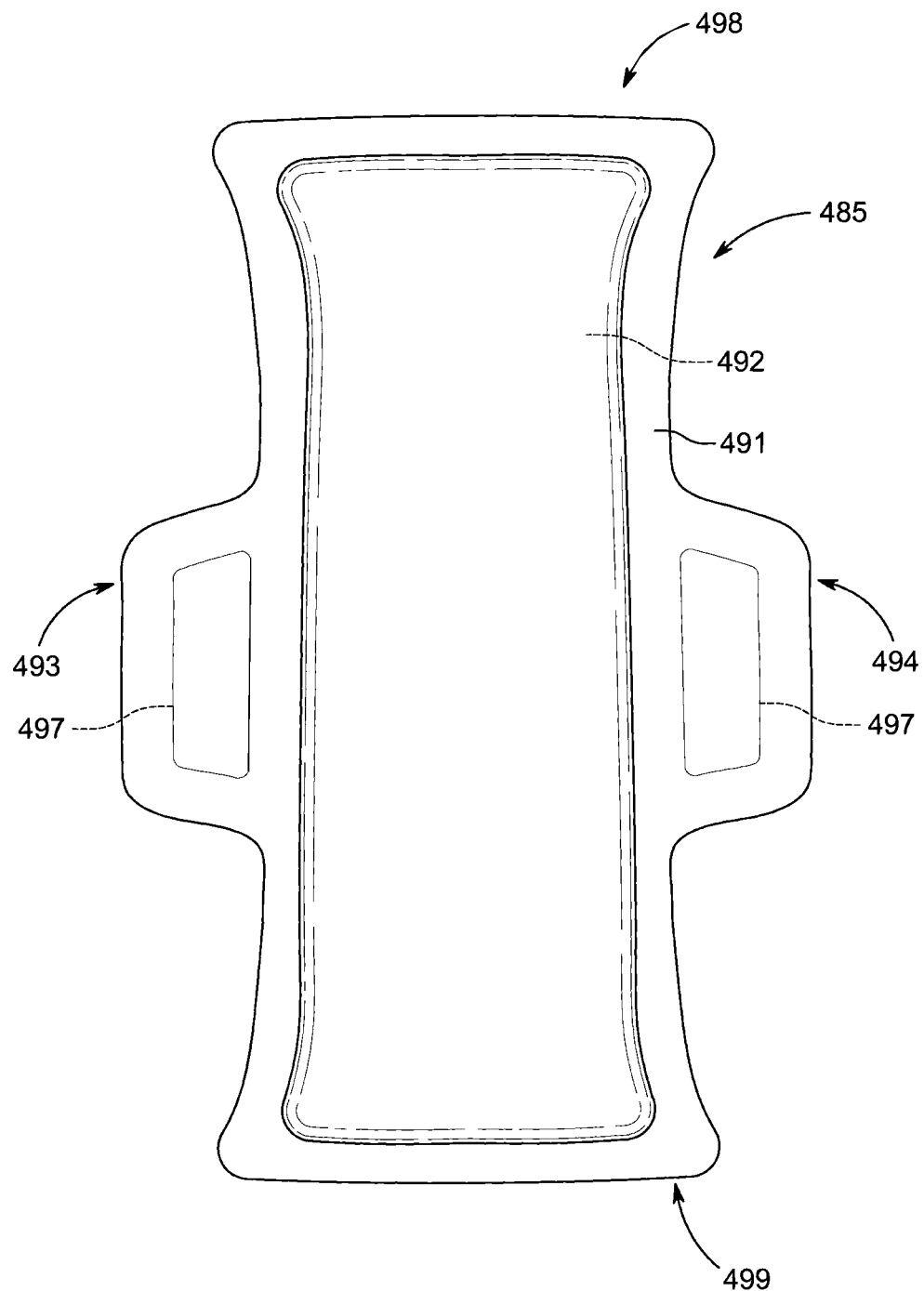
FIG. 10 is a top plan view of the incontinence pad from FIGS. 6-9.

The backing layer may include a pair of side flanges 494, 495 that are sized to at least partially wrap around the sling body 480 and the perimeter binding 482 and attach to an underside 496 of the sling body 480 as shown in FIGS. 9 and 10. The side flanges 494, 495 may also be fitted with adhesive strips 497 that are similar to adhesive patches 487, 489 to retain the side flanges 494, 495 to the underside 496 of the sling body 480.

Figure 11:
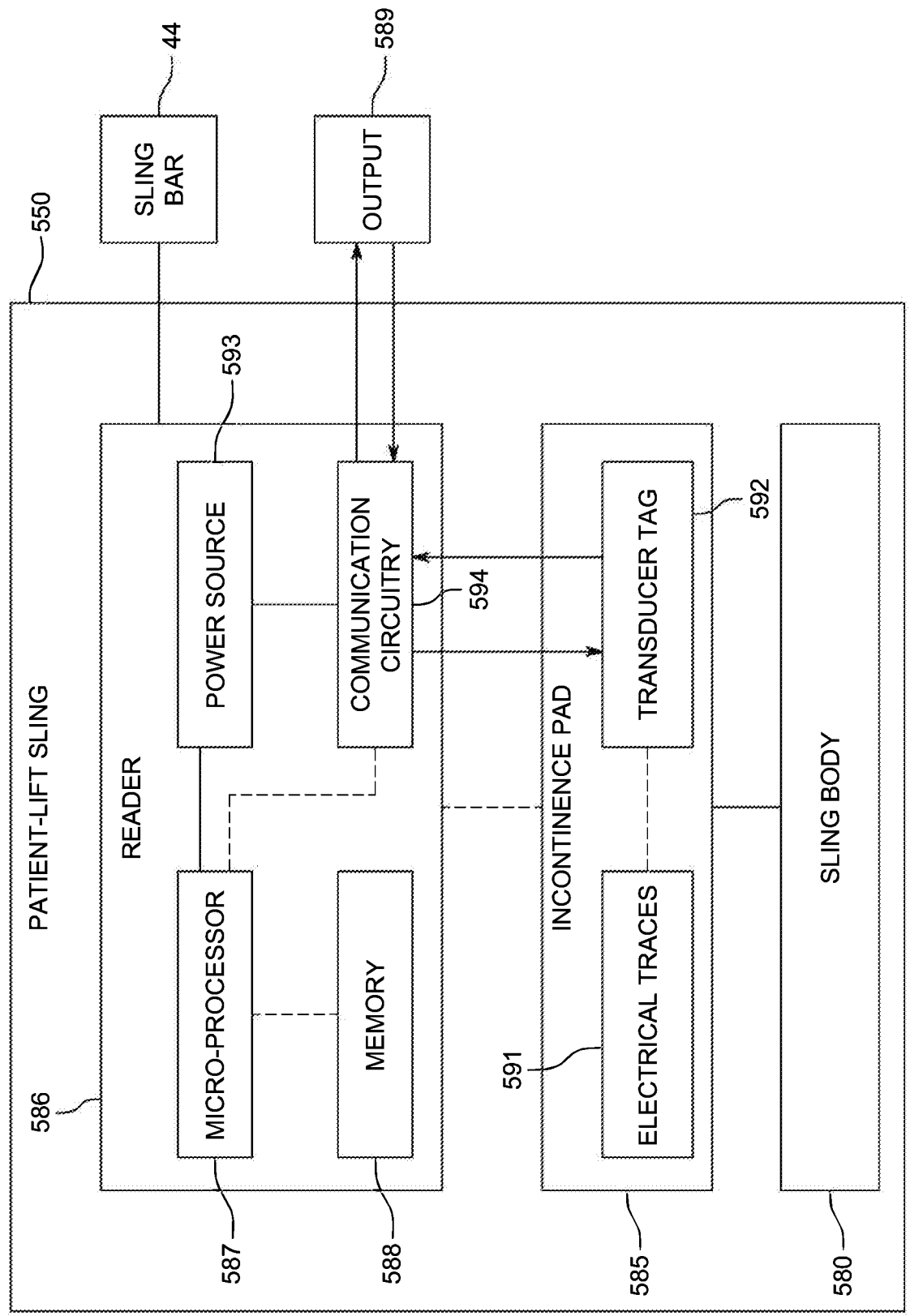
FIG. 11 is a diagrammatic view of another embodiment of a patient-lift sling having a sling body, an incontinence pad coupled to the sling body, and a reader configured to communicate with a transponder tag in the incontinence pad and provide an output in response to an incontinence event.

Another embodiment of a patient-lift sling 550 that is similar to patient-lift sling 450 except that patient-lift sling 550 is fitted with an incontinence pad 585 is configured to detect the presence of moisture and provide an output or alert 589 as shown diagrammatically in FIG. 11. The patient-lift sling 550 further includes a reader 586 that has a microprocessor 587, a memory storage device 588, a power source 593, and communication circuitry 594. The memory-storage device 588 stores instructions therein that, when executed by the microprocessor 587, communicates with the incontinence pad 585 and produces the output 589 in response to moisture being present on the incontinence pad 585. In one example, the output 589 is a notification that an incontinence event has occurred on the incontinence pad 585. The notification may be presented either visually or audibly on a mobile device, monitor, nurse call station or another suitable location to indicate to a caregiver that the incontinence pad has been soiled and should be replaced.

The reader 586 may communicate with one or more of the devices described above using either a wired or a wireless connection.

The communication circuitry 594 may include a transceiver and one or more antennas coupled to the transceiver to wirelessly send and receive signals from one or more of the devices described above. When an incontinence event is detected, the event may be relayed and stored in a patient's electronic medical record (EMR) to automatically document the event. Signals indicating that the pad is dry may also be stored in the patient's EMR with accompanying time stamps, if desired. Various types of wireless signals such as RFID, WiFi, Bluetooth, and Ultra-wideband (UWB) and corresponding readers and tags that communicate with such signals may be used with sling 550.

The incontinence pad 585 includes electrical traces 591 that extend through the incontinence pad 585 to sense the presence of fluid therein as shown in FIG. 11. The electrical traces 591 are electrically coupled to a transponder tag 592 that emits a signal which is received by the communication circuitry 594 of the reader 586. The transponder tag 592 may communicate with the communication circuitry 594 of the reader 586 using either a wired or a wireless connection. The incontinence pad 585 may be passively or actively operated to emit the signal from the transponder tag 592 and analyzed by the reader 586 to determine if moisture is present on the incontinence pad 585.

The transponder tag 592 in the illustrative embodiment is a passive radio-frequency identification (RFID) tag. The transponder tag 592 is periodically excited by the reader 586 located in proximity to the transponder tag 592 which causes the transponder tag 592 to emit a signal that can be used by the reader 586 to interrogate the tag 592. The tag 592 replies to the interrogation with data that is indicative of a status of the electrical traces 591. For example, the transponder tag 592 may reply with a first signal when there is no moisture on the electrical traces 591 and a second signal when there is moisture on the electrical traces 591. In this way, the reader 586 uses the data to passively determine if moisture is present on the incontinence pad 585.

Figure 12:
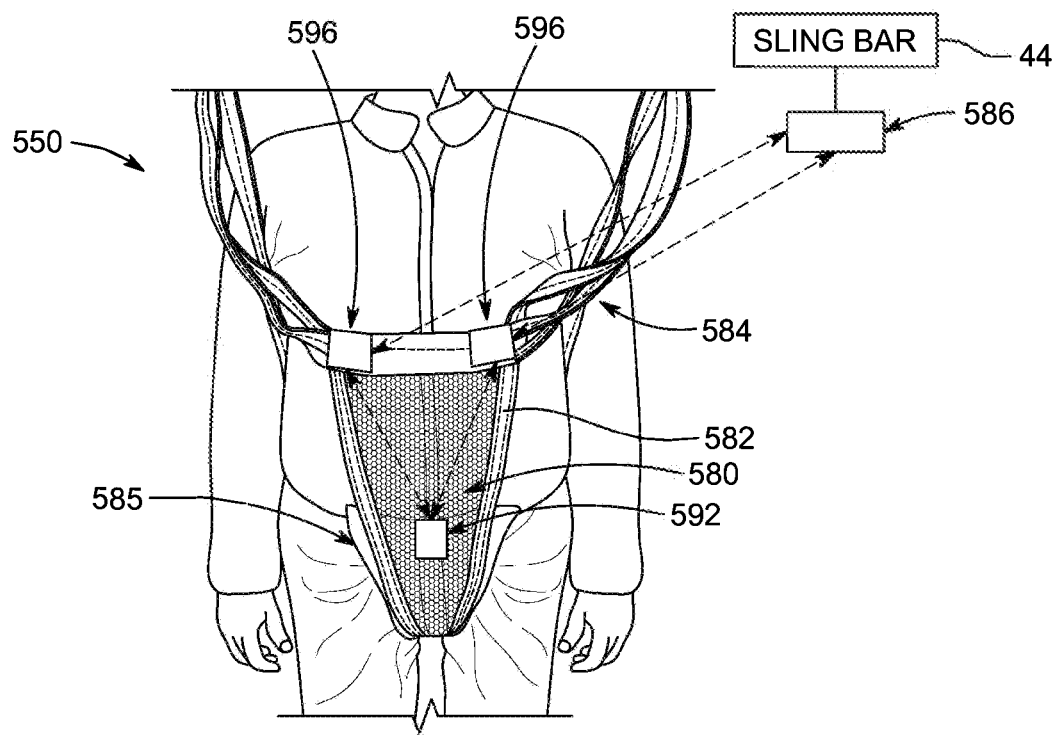
FIG. 12 is a front perspective view of a patient-lift sling having an incontinence pad with a transponder tag and a pair of antennas to communicate with a remote reader.
Figure 13:
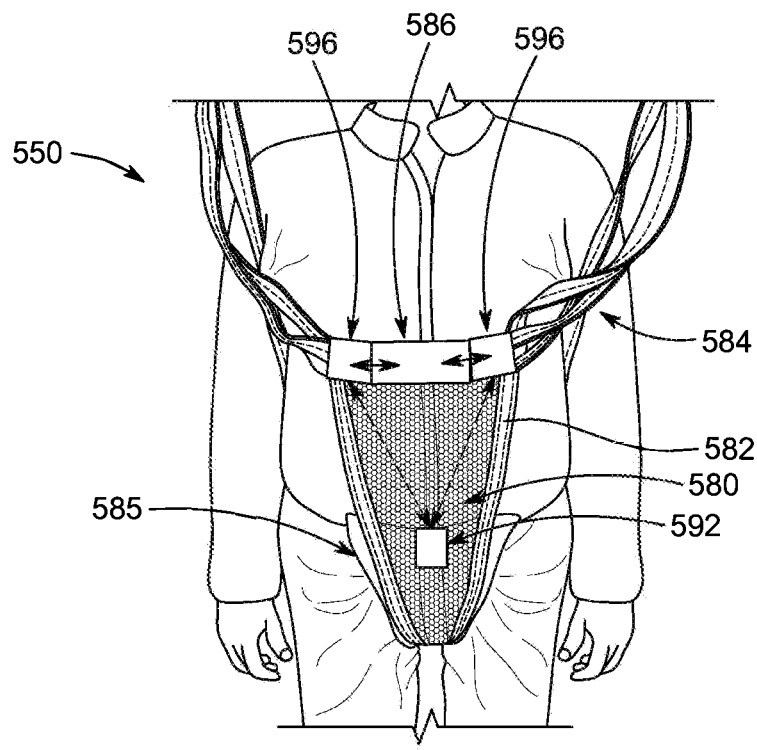
FIG. 13 is a front perspective view of a patient-lift sling having an incontinence pad with a transponder tag, a pair of antennas, and a reader coupled directly to the patient-lift sling.

The reader 586 may be coupled to the sling bar 44 as shown in FIGS. 11 and 12. Alternatively, the reader 586 may be coupled directly to the sling body 580, a perimeter binding 582, or an attachment loop 584 as shown in FIG. 13. In other embodiments, the reader may be coupled to another part of the patient-lift system or to a structure in the room where the patient-lift system is located such as a wall or the ceiling. The transponder tag 592 is coupled to the electrical traces 591 at a forward end of the incontinence pad 585 within a reception range of the reader so that the patient does not obstruct the signals being emitted by reader 586 and/or the transponder tag 592 as shown in FIGS. 12 and 13. The incontinence pad 585 may further include a second transponder tag on a rear end of the incontinence pad 585 thereby reasonably ensuring that at least one transponder tag is within reception range of the reader 586 at all times which thereby increases an effective range of the signals being transmitted between the incontinence pad 585 and the reader 586. Antennas 596 may be coupled to the sling 550 to detect the signals from the transponder tag 592 and communicate them to the reader 586 as well as being used by the reader 586 to energize the transponder tag 592. The antennas 596 wirelessly sense the signal from the transponder tag 592 as suggested in FIGS. 12 and 13.

In some embodiments, the transponder tag 592 is an active tag that may actively emit a signal in response to moisture forming a closed circuit between at least two of the electrical traces 591. The signal from the active tag 592 is received by the communication circuitry 594 which provides the output 589 to indicate that moisture has been detected on the incontinence pad 585. The incontinence pad 585 may include an on-board battery to supply power for the active tag 592 so that it can actively send the signals to the reader 586.

Although this disclosure refers to specific embodiments, it will be understood by those skilled in the art that various changes in form and detail may be made without departing from the subject matter set forth in the accompanying claims.

The invention claimed is:

1. A patient-lift sling comprising
   a sling body configured to support a patient,
   a perimeter binding that extends around an outer edge of the sling body,
   a plurality of attachment straps coupled to the perimeter binding, and
   an incontinence pad coupled removably to the sling body by a plurality of adhesive strips that extend parallel with one another along a length of the sling body,
   wherein the sling body includes at least one layer of warp-knit fabric that has a first stiffness value and the perimeter binding and each of the attachment straps include at least one layer of woven fabric that has a second stiffness value greater than the first stiffness value.

2. The patient-lift sling of claim 1, wherein the sling body includes a body section configured to support at least a portion of a patent's upper body, a first leg section configured to support one of the patient's legs, and a second leg section configured to support another of the patient's legs.

3. The patient-lift sling of claim 2, wherein the sling body includes a first layer of warp-knit fabric, a second layer of warp-knit fabric at least partially spaced apart from the first layer of warp-knit fabric, and an inner layer of spacer material arranged between the first and second layers of warp-knit fabric.

4. The patient-lift sling of claim 3, wherein the spacer material includes an upper-body portion located in the body section, a first leg portion coupled with the upper-body section and located in the first leg section, and a second leg portion coupled with the upper-body section and located in the second leg section.

5. The patient-lift sling of claim 4, wherein the sling body further comprises a plurality of stitches that extend through the first layer of warp-knit fabric, the spacer material, and the second layer of warp-knit fabric, and wherein the stitches are oriented relative to one another to maximize flexibility of the sling body.

6. The patient-lift sling of claim 5, wherein the plurality of stitches includes a plurality of vertically oriented stitches located on the body section, a plurality of horizontally-oriented stitches located on the first and second leg sections, and at least one diagonally-oriented stitch located between the vertically-oriented stitches and the first leg section and between the vertically-oriented stitches and the second leg section.

7. The patient-lift sling of claim 6, wherein the vertically-oriented stitches include a first vertical stitch that is configured to align with a patient's spine.

8. The patient-lift sling of claim 7, wherein the vertically-oriented stitches further includes a second vertical stitch that is configured to align with the patient's left shoulder blade and a third vertical stitch that is configured to align with the patient's right shoulder blade.

9. The patient-lift sling of claim 8, wherein the sling body has a first color and each of the vertically-oriented stitches has a second color different than the first color.

10. The patient-lift sling of claim 2, wherein the plurality of attachment straps includes a first set of body-section loops coupled to the perimeter binding at each upper corner of the body section and a second set of body-section loops coupled to the perimeter binding and spaced inward from the first set of body-section loops.

11. The patient-lift sling of claim 2, further comprising a body-section adjustment system configured to change a width of the body section to raise and lower a patient's head relative to the body section.

12. The patient-lift sling of claim 11, wherein body section has a first upper corner and a second upper corner and the adjustment system includes a first extensible-strap unit coupled to the perimeter binding and interconnecting the first outer corner of the body section and a first point on the perimeter binding between the first upper corner and the second upper corner and a second extensible-strap unit coupled to the perimeter binding and interconnecting the second outer corner of the body section and a second point on the perimeter binding between the first point and the second upper corner.

13. The patient-lift sling of claim 12, wherein the first and second extensible-strap units each include a first strap coupled to one of the first upper corner and the second upper corner, a second strap coupled to a corresponding one of the first point and the second point and a buckle coupled to the first strap and the second strap and configured to allow adjustment of at least one of the first strap and the second strap to raise and lower a head section of the sling body.

14. The patient-lift sling of claim 2, wherein the body section is formed to include a first cutout along a first lateral side of the body section and a second cutout along a second lateral side of the body section.

15. The patient-lift sling of claim 14, wherein an edge of the body section defining the first cutout and the second cutout is spaced apart from the perimeter binding to provide a first handle on the first lateral side and a second handle on the second lateral side.

16. The patient-lift sling of claim 15, wherein the first handle and the second handle are the only handles on the body portion.

17. The patient-lift sling of claim 1, wherein the sling body, the perimeter binding, and the plurality of attachment straps are made from a material consisting of polyester.

18. The patient-lift sling of claim 1, wherein the incontinence pad includes at least one electrical trace fitted within the incontinence pad and a transponder tag coupled to the at least one electrical trace to provide a signal in response to moisture being present on the incontinence pad to notify a caregiver that an incontinence event has occurred.

19. The patient-lift sling of claim 1, wherein the incontinence pad includes a first side flange and a second side flange on an opposite side of the incontinence pad as the first side flange and wherein the first and second side flanges are coupled to an underside of the sling body by an adhesive strip.

* * * * *